United States Patent [19]

Baldwin et al.

[11] 4,259,341

[45] Mar. 31, 1981

[54] DI- AND TRI-SUBSTITUTED THIAZOLES

[75] Inventors: John J. Baldwin; Gerald S. Ponticello, both of Lansdale, Pa.

[73] Assignee: Merck & Co., Inc., Rahway, N.J.

[21] Appl. No.: 960,280

[22] Filed: Nov. 13, 1978

Related U.S. Application Data

[63] Continuation of Ser. No. 802,403, Jun. 1, 1977, abandoned.

[51] Int. Cl.³ .......................................... C07D 277/20
[52] U.S. Cl. ................................... 424/270; 548/186; 548/187; 548/183
[58] Field of Search ........... 260/302 R, 302 S, 302 H; 548/183, 186, 187; 424/270

[56] References Cited

U.S. PATENT DOCUMENTS

| | | | |
|---|---|---|---|
| 3,850,945 | 11/1974 | Edwards | 260/302 R |
| 3,850,946 | 11/1974 | Edwards | 260/302 R |
| 3,850,947 | 11/1974 | Edwards | 260/302 R |
| 3,897,441 | 7/1975 | Edwards | 260/302 R |
| 3,897,442 | 7/1975 | Edwards | 260/302 R |
| 3,932,400 | 1/1976 | Hibino et al. | 260/247.1 M |

*Primary Examiner*—Nicholas S. Rizzo
*Attorney, Agent, or Firm*—Daniel T. Szura; Harry E. Westlake, Jr.

[57] ABSTRACT

Di- and tri-substituted thiazoles, one substituent being a 3-amino-2-OR-propoxy group are disclosed. The thiazoles have β-adrenergic blocking activity.

18 Claims, No Drawings

DI- AND TRI-SUBSTITUTED THIAZOLES

This is a continuation of copending U.S. application Ser. No. 802,403, filed June 1, 1977 now abandoned.

BACKGROUND OF THE INVENTION

The present invention involves novel di- and tri-substituted thiazoles having pharmaceutical activity as $\beta$-adrenergic blocking agent.

Thiazoles having an aminohydroxypropoxy substituent in the 2-position with or without a specific additional substituent in the 4 or 5-position, are known and are taught to have $\beta$-adrenergic stimulating activity (U.S. Pat. No. 3,850,945). Thiazoles having an aminohydroxypropoxy substituent in the 4 or 5-position with no additional sbustitution are also known and are taught to have $\beta$-adrenergic stimulating activity (U.S. Pat. Nos. 3,850,947, 3,850,946). Thiazoles having the aminohydroxypropoxy substituent in the 2-position with an aminocarbonyl, formamido, substituted oxycarbonyl amino group in the 4 or 5-position, are known and taught to have $\beta$-adrenergic blocking activity (U.S. Pat. No. 3,897,411). Thiazoles having the following formula

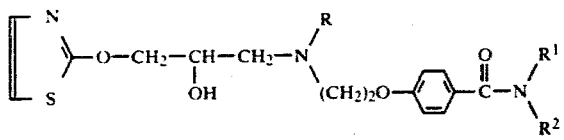

are known and are taught to be $\beta$-adrenergic blocking agents. (U.S. Pat. No. 3,897,442). Thiazoles of the formula

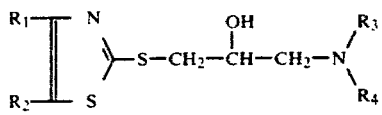

are known and are taught to block $\beta$-adrenergic receptors (U.S. Pat. No. 3,932,400).

Novel di- and tri-substituted thiazoles having a 4(3-amino-2-OR-propoxy) substituent have been discovered. The thiazoles are active as $\beta$-adrenergic blocking agents.

SUMMARY OF THE INVENTION

Di- and tri- substituted thiazoles having a 4(3-amino-2-OR-propoxy) group and their pharmaceutical use.

DESCRIPTION OF THE PREFERRED EMBODIMENTS

An embodiment of the present invention is compounds having the formula

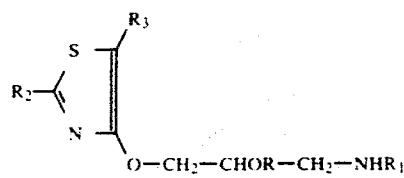

and pharmaceutically acceptable salts thereof, wherein

R is hydrogen or $C_2$-$C_{12}$acyl,
$R_1$ is $C_1$-$C_{12}$alkyl,
$R_2$ is hydrogen, $CF_3$, $C_6$-$C_{12}$ carbocyclic aryl, 6-membered-N-heteroaryl, $C_1$-$C_6$ alkyl, $C_1$-$C_6$ alkylthio, $C_1$-$C_6$ alkylsulfinyl, $C_1$-$C_6$ alkylsulfonyl, thienyl and furfuryl,
$R_3$ is $C_1$-$C_6$ alkyl, —$COOC_1$-$C_6$ alkyl, $COOC_6$-$C_{12}$ aryl, cyano, $C_6$-$C_{12}$ carbocyclic aryl, $CF_3$ or

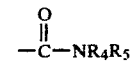

wherein $R_4$ and $R_5$ are independently selected from H and $C_1$-$C_6$ alkyl or are joined forming

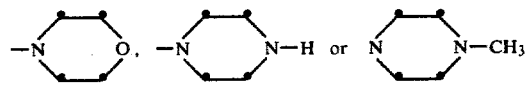

provided that when $R_2$ is phenyl, $R_3$ is other than $C_1$-$C_6$ alkyl or $COOC_1$-$C_6$ alkyl.

The pharmaceutically acceptable salts are the acid addition salts of the formula I free base. Suitable acids include organic as well as inorganic acids. Examples of useful organic acids are carboxylic acids such as acetic acid, pamoic acid, maleic acid, succinic acid, citric acid, tartaric acid, oxalic acid, malic acid, pivalic acid, heptanoic acid, lauric acid, propanoic acid, pelargonic acid, oleic acid and the like, and non-carboxylic acids such as isethionic acid. Examples of useful inorganic acids are the hydrogen halides i.e., HCl, HBr, HI, phosphoric acid, sulfuric acid, and the like. The hydrohalide salts especially the hydrocylorides and maleic acids, especially the hydrogen maleate, are preferred.

R may be hydrogen or $C_2$-$C_{12}$ acyl. The $C_2$-$C_{12}$ acyl groups include alkanoyl groups such as acetyl, pivaloyl, dodecanoyl, hexanoyl, succinoyl and the like—and carbocyclic aroyl groups such as benzoyl, 1- or 2-naphthoyl, p-methylbenzoyl, p-phenylbenzoyl and the like. The $C_2$-$C_6$ alkanoyl and benzoyl groups are preferred acyl groups. Hydrogen is a most preferred R group.

The $R_1$ substituent includes $C_1$-$C_{12}$ alkyl groups and preferably the $C_1$-$C_6$alkyl groups. The alkyl groups are exemplified by methyl, $C_{12}H_{25}$, hexyl, 2-ethylhexyl, isopropyl, sec-butyl, heptyl and the like. The $C_{3-4}$ branched chain alkyl $R_1$ groups are more preferred, with t-butyl being a most preferred group.

$R_2$ includes H, $CF_3$, $C_6$-$C_{12}$ carbocyclic aryl such as phenyl, monosubstituted phenyl e.g. p-tolyl, o-halophenyl, p-nitrophenyl, p-methoxyphenyl and p-halophenyl; indanyl; 1- or 2-naphthyl and the like, 6-membered-N-heteroaryl such as 2-, 3- or 4-pyridyl, pyridazinyl, pyrazinyl, pyrimidinyl and the like; thienyl, furfuryl $C_1$-$C_6$alkyl, e.g. methyl, n-hexyl, isopropyl, sec-butyl, ethyl and the like, $C_1$-$C_6$ alkylthio, and the sulfinyl and sulfonyl derivatives exemplified by $C_2H_5$—S, $C_4H_9$—SO, $C_6$—$H_{13}$—$SO_2$, $CH(CH_3)_2$—$SO_2$, $CH_3$—SO, t-butyl-S and the like. Preferred $R_2$ groups are hydrogen, $C_1$-$C_6$alkyl and $C_1$-$C_6$-alkylthio, especially $CH_3$—S.

The $R_3$ substituent includes $CF_3$, $C_1$-$C_6$ alkyl, CN, $C_6$-$C_{12}$ carbocyclic aryl such as phenyl, carboxylic acid esters and amides. The $C_1$-$C_6$ alkyl group is exemplified by $CH_3$, isopropyl, and the like. The ester group is $C_1$-$C_6$-alkylester exemplified by —$COOCH_3$, —COOC$_6$H$_{13}$, —COOCH(CH$_3$)$_2$, —COOC$_2$H$_5$ and the like and C$_6$-C$_{12}$ arylester, preferably carbocyclic aryl, exemplified by C$_6$H$_5$—OOC, p—CH$_3$—C$_6$H$_4$—OOC—, p—C$_6$H$_5$—C$_6$H$_4$—OOC—, C$_9$H$_9$—OOC— and the like. The amide group includes —CONH$_2$, C$_1$-C$_6$ substituted amide groups such as —CON(CH$_3$)$_2$, —CON(C$_6$H$_{13}$)$_2$, —CONHC$_2$H$_5$, —CON (sec. butyl)$_2$ and the like and carbonyl heterocyclic groups such as

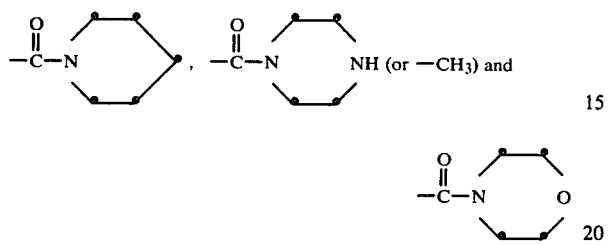

Of the R$_3$ groups, CN, CF$_3$ and amide, especially CONH$_2$, are preferred.

The formula I compounds have a chiral center, (at the 2 carbon in the propoxy substituent) which confers optical activity. The optical isomers are designated conventionally as L and D, l and d, + and −, S and R or by combinations of these symbols. Where the formula or compound name herein carries no specific designation, the formula or name includes the individual isomers, the mixtures thereof and racemates.

The thiazole compounds which are preferred have the formula

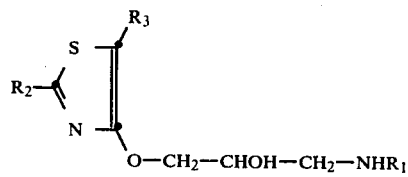

Formula II compounds where R$_2$ is H, C$_1$-C$_6$ alkylthio, preferably CH$_3$—S—, or said heteroaryl groups, especially pyridyl, R$_3$ is CN, CF$_3$, amide, C$_1$-C$_6$ alkyl or said ester group and R$_1$ is C$_1$-C$_6$ alkyl especially C$_3$-C$_4$ branched alkyl are more preferred. In most preferred formula II compounds, R$_2$ is said alkylthio or heteroaryl, R$_3$ is CN, CF$_3$, CONH$_2$, C$_1$-C$_6$alkyl or said ester and R$_1$ is C$_3$-C$_4$ branched alkyl.

Another preferred group of thiazoles has the formula

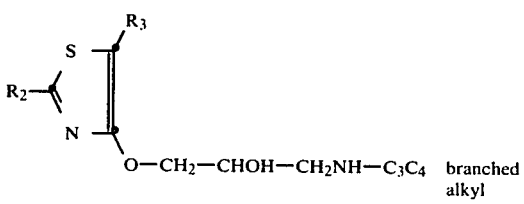

where R$_2$ is H, C$_1$-C$_6$ alkyl, C$_1$-C$_6$ alkylthio or pyridyl, R$_3$ is CN, CF$_3$, C$_1$-C$_6$ alkyl or CONH. In more preferred formula III thiazoles, said branched alkyl is tert.-butyl, R$_2$ is H, CH$_3$, CH$_3$S or pyridyl, and R$_3$ is CN, CH$_3$, CONH$_2$ or CF$_3$ and the thiazoles where said branched alkyl is tert.-butyl, R$_2$ is H, CH$_3$S or pyridyl and R$_3$ is CN or CONH$_2$ are particularly preferred.

Of the optical isomers those having the S-isomer configuration are preferred.

The thiazoles of the present invention have β-adrenergic blocking activity. This was determined in an in-vivo test using dogs as the test animals. In this test, representative thiazole compounds, were found to counteract the β-adrenergic stimulating effect of isoproterenol.

Certain of the present thiazoles also exhibit an antihypertensive effect of immediate onset when administered to a spontaneously hypertensive (SH) rat. Representative of such compounds are those having the formula

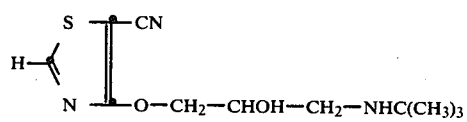

and

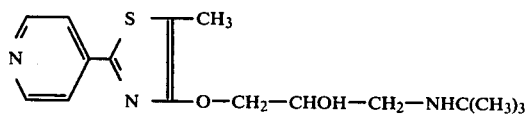

The present thiazoles also show random vasodilator activity.

The present thiazole compounds will effect β-adrenergic blockade in humans. This β-adrenergic blocking effect is useful in the therapeutic treatment of various cardiovascular conditions such as angina pectoris, arrhythmia etc. In administering these formula I compounds for their β-adrenergic blocking effect, the daily dosage may range from about 1.5 mg. to about 3000 mg. Preferred daily dosages are about 6.5 mg. to about 200 mg. Conventional dosage forms suitable for oral as well as parenteral, e.g. intravenous, intraperitoneal etc., administration are used. Oral dosage forms include tablets, capsules, troches, liquid formulations e.g. solutions, emulsions, elixirs, etc.—parenteral dosage forms include liquid formulations especially solutions. The compositions are prepared using conventional procedures and compounding ingredients such as starch, sterile water, flavoring additives, antioxidants, binders, vegetable oils, sweetening agents, glycerine and the like.

Thiazoles which exhibit the immediate onset antihypertensive activity are useful for treating hypertensive humans at daily dosages ranging from about 100 to about 3000 mg. administered in oral or parenteral dosage forms.

The present thiazoles can be prepared by any convenient process.

One such process involves the coupling of a suitably substituted thiazole with a suitably substituted oxazolidine and hydrolyzing the reaction product obtained. This process is illustrated by the following set of reaction equations:

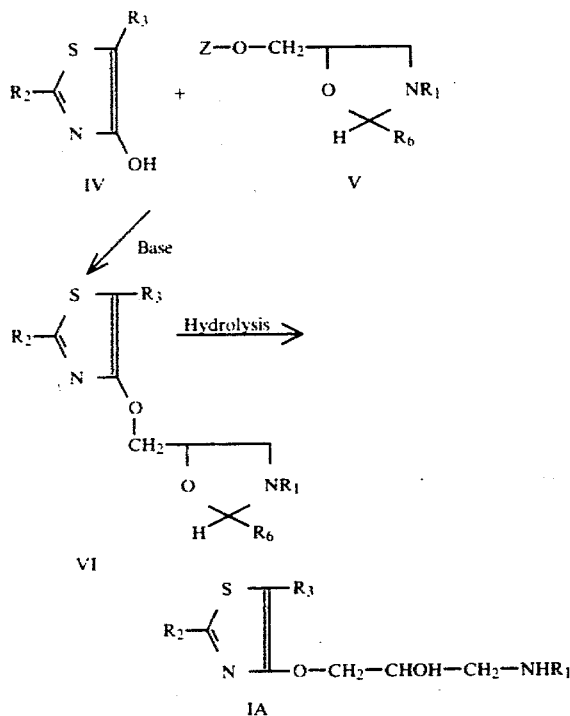

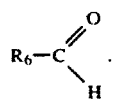

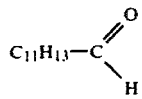

Z is an alkyl or arylsulfonyl group. Examples of sulfonyl groups are $CH_3-SO_2-$, $C_6H_5-SO_2-$, $NO_2-C_6H_4-SO_2-$, $p-CH_3-C_6H_4-SO_2-$, mesitylene$-SO_2-$, $CH_3O-C_6H_4-SO_2-$, trichlorobenzene$-SO_2-$, $C_{16}H_{33}-SO_2-$ and the like. Suitable bases are alkali metal bases such as $K_2CO_3$, $K-O-C(CH_3)_3$, NaH, organolithiums e.g. phenyllithium, n-butyllithium, lithium diisopropyl amide and the like.

$R_6$ is hydrogen or other $C_1-C_{12}$ alkyl or $C_6-C_{12}$ carbocyclic aryl residue of any suitable aldehyde $$R_6-C\overset{O}{\underset{H}{\diagup}}$$

Examples of suitable aldehydes are the aryl aldehydes such as benzaldehyde, naphthaldehyde, 4-phenylbenzaldehyde, furfural, bromobenzaldehyde, tolualdehyde, mesitaldehyde and the like, or an alkanal such as acetaldehyde, butyraldehyde $$C_{11}H_{13}-C\overset{O}{\underset{H}{\diagup}}$$

and the like. The process for preparing oxazolidines where Z is hydrogen (and a related coupling reaction) is disclosed in U.S. Pat. Nos. 3,718,647 and 3,657,237 and to the extent necessary the pertinent disclosure is incorporated herein by reference.

The coupling reaction can be carried out at temperatures ranging from about 0° C. to about 130° C. A temperature range of about 50° C. to about 130° C. is preferred. The reaction is generally carried out in a solvent. Any suitable solvent may be used. Examples of useful solvents are dimethylformamide, dimethylsulfoxide, hexamethylphosphoramide, tert.butanol, dioxane, toluene, acetone and the like. The hydrolysis is carried out using a conventional acid system e.g. by treatment with a solution of any suitable acid such as HCl, $H_2SO_4$, $CH_3COOH$ and the like. The hydrolysis product can be directly obtained as the salt of the acid used for the hydrolysis. Ordinarily, the product IA is recovered as the free base after conventional neutralization of the salt.

The coupling reaction is ordinarily carried out at atmospheric pressure. Higher pressures may be used if desired.

When a racemic oxazolidine (formula V) is used as a reactant, the product is obtained as a racemate. The racemate may be separated into its individual enantiomers by conventional resolution techniques.

When $R_6$ in the oxazolidine (e.g. formula V or VI) is other than hydrogen, in addition to the chiral center at oxazolidine position 5 there is a second chiral center at position 2. However, whenever an oxazolidine is designated e.g. as (S), (R) or (R,S), this designation refers only to the optical configuration around the carbon atom at the 5 position.

By using a single optical isomer of the formula V oxazolidine in the above reaction the thiazole product (IA) may be obtained directly as a single enantiomer. This provides a convenient way for directly preparing individual isomers of the present thiazoles.

Thiazoles represented by formula I wherein R is other than hydrogen are conveniently prepared by treating the corresponding thiazole where R is hydrogen with an appropriate acylating agent such as an acyl halide, e.g. undecanoyl chloride, pivaloyl chloride, benzoylchloride, p-methoxybenzoyl chloride, an anhydride e.g. acetic anhydride and the like. The reaction is illustrated by the following equation:

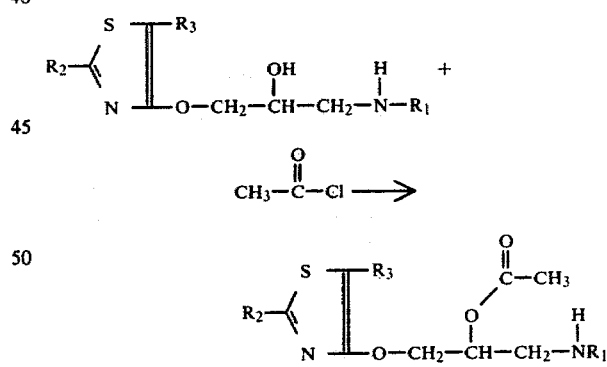

The compounds of the present invention also include the pharmaceutically acceptable salts of the novel thiazoles. These salts are conveniently prepared e.g. by treating the thiazole with an appropriate amount of a useful acid, generally in a suitable solvent.

Additional processes for preparing thiazoles with certain other substituents are illustrated by the following equation sequences. Conventional reaction conditions are employed. The symbol L represents the $-CH_2-CHOR-CH_2-NR_1$ group.

Sequence 1

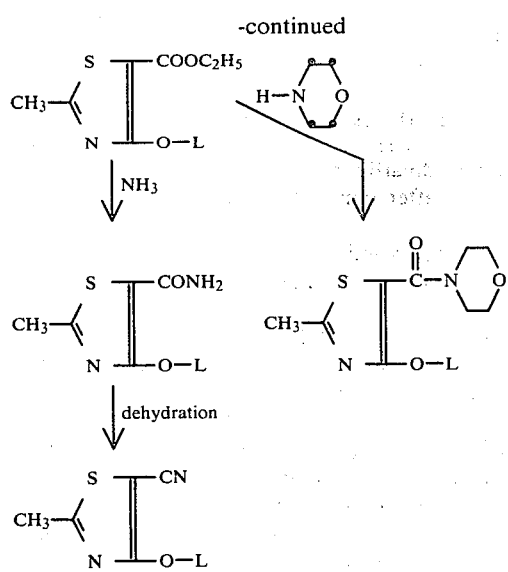

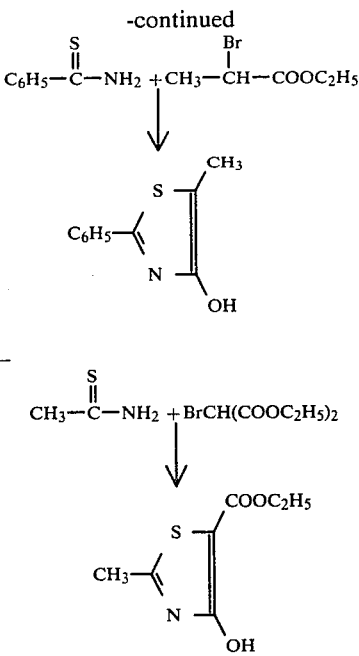

Reaction B

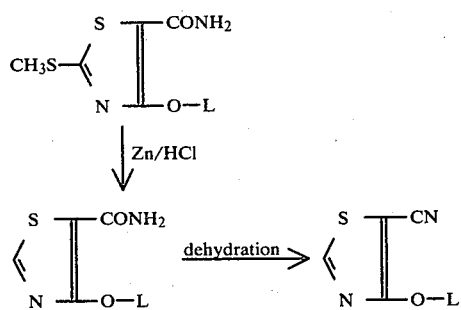

The following examples illustrate preparation of representative thiazoles of the present invention. All temperatures are in °C.

EXAMPLE 1

(S) 5-Methyl-2-phenyl-4(3-tert.butylamino-2-hydroxypropoxy)thiazole hydrogen maleate salt To a stirred solution of (S) 2-phenyl-3-tert.-butylamino-5-hydroxymethyloxazolidine (2.5 g., 0.01 m) and dry pyridine (5 ml.) is added portionwise p-toluenesulfonyl chloride (2.0 g., 0.011 m), while maintaining the temperature of the reaction below 30° C. After the addition, the mixture is stirred at room temperature for 3 hours. To the solid mixture is added a solution of $K_2CO_3$ (1.4 g., 0.01 m) in $H_2O$ (10 ml.) and the solution extracted with $CHCl_3$ (3×25 ml.). The organic layer is dried over $Na_2SO_4$, filtered and concentrated to dryness below 50° C. to yield the tosylate of (S) 2-phenyl-3-tert.butylamino-2-hydroxymethyloxazolidine which is used in the next step without further purification.

Into a dry flask under $N_2$ is added 4-hydroxy-5-methyl-2-phenylthiazole (1.91 g., 0.1 m), dimethylformamide (DMF) (20 ml.) and NaH (50% mineral oil, 0.5 g., 0.01 m). After stirring at room temperature for 15 minutes, the tosylate of (S) 2-phenyl-3-tert.-butylamino-5-hydroxymethyloxazolidine (0.01 m) in DMF (20 ml.) is added and the solution heated under reflux with stirring. After 12 hours, the solvent is removed under reduced pressure (1.5 mm). The residue is treated with 1 N HCl (100 ml.) and heated on a steam bath for ¾ hours. After cooling, the aqueous layer is extracted with ether (2×50 ml.), neutralized with saturated $Na_2CO_3$, and extracted with $CHCl_3$ (3×100 ml.). The organic layer is dried over $Na_2SO_4$, filtered and concentrated to dryness. The residue is chromatographed on silica gel 60 and the product eluted with 10% MeOH—$CHCl_3$. The crude product is crystallized with maleic acid in isopropanol (IPA)-MeOH to yield 0.25 g. (6%) of 5-methyl-2-

The thiazoles having an alkylsulfinyl or alkylsulfonyl substituent are prepared by oxidizing the corresponding $C_1$-$C_6$ alkylthio containing compound. Any suitable oxidizing agent, e.g. $H_2O_2$, may be used. The following equation illustrates the reaction

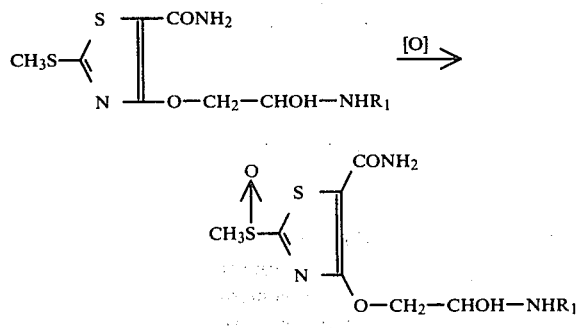

The 4-OH substituted thiazole intermediates used in the oxazolidine coupling reaction described above are prepared using conventional processes illustrated by the following equations:

Reaction A phenyl-4(3-tert.butylamino-2-hydroxypropoxy) thiazole hydrogen maleate salt, m.p. 174°-6° C.

EXAMPLE 2

(S)

5-Carbamoyl-2-phenyl-4-(3-tert.butylamino-2-hydroxypropoxy) thiazole hydrogen maleate salt A. Into a dry flask under $N_2$ is added ethyl 4-hydroxy-2-phenylthiazole-5-carboxylate (2.5 g., 0.01 m), DMF (20 ml.) and NaH (50% mineral oil, 0.5 g., 0.01 m). After stirring for 15 minutes, a solution of the tosylate of (S) 2-phenyl-3-tert.butylamino-5-hydroxymethyloxazolidine (0.01 m) in DMF (15 ml.) is added at 0°-4° C. and the solution heated with stirring at 100° C. After 15 hours, the solution is cooled to 0°-10° C., poured into $H_2O$ (100 ml.) and extracted with ether (3×100 ml.). The organic layer is extracted with 1 N HCl (2×50 ml.) and the acid layer added to NaOAc (8.2 g., 0.1 m). After 5 hours, the solution is extracted with ether (2×50 ml.). The aqueous layer is neutralized with saturated $Na_2CO_3$ and extracted with $CHCl_3$ (3×100 ml.). The organic layer is dried over $Na_2SO_4$, filtered and concentrated to dryness. The residue is chromatographed on alumina (activity grade II, E. Merck) and the product eluted with 25% hexane-$CHCl_3$. The crude product is crystallized with maleic acid in $CH_3CN$-ether to yield 0.7 g. (14%) of (S) ethyl-2-phenyl-4-(3-tert.butylamino-2-hydroxypropoxy)-thiazole-5-carboxylate hydrogen maleate, m.p. 165°-7° C.

B. A mixture of (S) ethyl-2-phenyl-4-(3-tert.butylamino-2-hydroxypropoxy)thiazole-5-carboxylate, obtained by neutralizing the product from A., (4.7 g., 0.012 m), MeOH (90 ml.) and liquid $NH_3$ (22 g.) is heated at 100° C. in a sealed tube. After 24 hours, the reaction mixture is concentrated to dryness. The residue is chromatographed on alumina (activity grade II, E. Merck) and the product eluted with $CHCl_3$. The crude product is crystallized with maleic acid in IPA to yield 1.65 g. (30%) of (S) 5-carbamoyl-2-phenyl-4-(3-tert.butylamino-2-hydroxypropoxy) thiazole hydrogen maleate salt, m.p. 184°-5° C.

EXAMPLE 3

(S)

5-Cyano-2-phenyl-4-(3-tert.butylamino-2-hydroxypropoxy) thiazole hydrogen maleate salt hemihydrate To triphenylphosphine oxide (2.25 l g., 0.008 m) in $CH_2Cl_2$ (20 ml.) is added dropwise at 0°-4° C. a solution of triflic anhydride (1.4 g., 0.0089 m) in $CH_2Cl_2$ (15 ml.). After 15 minutes, (S) 5-carbamoyl-2-phenyl-4-(3-tert.butylamino-2-hydroxypropoxy)thiazole (1.4 g., 0.004 m) is added and the solution allowed to warm to room temperature. After stirring overnight at room temperature, the mixture is poured into saturated $Na_2CO_3$ (100 ml.) and the solution extracted with $CH_2Cl_2$ (3×400 ml.). The organic layer is dried over $Na_2SO_4$, filtered and concentrated to dryness. The residue is chromatographed on alumina (activity grade II, E. Merck) and the product eluted with $CHCl_3$. The crude product is crystallized with maleic acid in IPA to yield 0.3 g. (16%) of (S) 5-cyano-2-phenyl-4-(3-tert.butylamino-2-hydroxypropoxy)thiazole hydrogen maleate salt hemihydrate, m.p. 204°-6° C.

EXAMPLE 4

(S)

Ethyl-2-methylthio-4-(3-tert.butylamino-2-hydroxypropoxy)thiazole-5-carboxylate hydrogen maleate salt Into a dry flask under $N_2$ is added ethyl-4-hydroxy-2-methylthiazole-5-carboxylate (20 g., 0.091 m), DMF (200 ml.) and NaH (50% mineral oil, 5.0 g., 0.104 m). After stirring for 15 minutes, a solution of the tosylate of (S)-2-phenyl-3-tert.butylamino-5-hydroxymethyloxazolidine (0.106 m) in DMF (150 ml.) is added at room temperature and the solution heated on a steam bath with stirring. After 15 hours, the solution is cooled to 0°-10° C., poured into $H_2O$ (1 l.) and extracted with ether (3×300 ml.). The organic layer is washed with $H_2O$ (2×150 ml.) and 1 N HCl (3×233 ml.). The acid layer is added to NaOAc.3$H_2O$ (95 g., 0.7 m). After 5 hours, the solution is extracted with ether (2×200 ml.), neutralized with saturated $Na_2CO_3$ and extracted with $CHCl_3$ (3×300 ml.). The organic layer is dried over $Na_2SO_4$, filtered and concentrated to dryness. The residue is chromatographed on alumina (activity grade II, E. Merck) and the product eluted with $CHCl_3$. The crude product is crystallized with maleic acid in IPA-$Et_2O$ to yield 8.8 g. (21%) of (S) ethyl 2-methylthio-4-(3-tert.butylamino-2-hydroxypropoxy)thiazole-5-carboxylate hydrogen maleate salt, m.p. 114°-116° C.

EXAMPLE 5

(S)

5-Carbamoyl-2-methylthio-4-(3-tert.butylamino-2-hydroxypropoxy)thiazole hydrogen maleate salt Using the same procedure described in Example 2B, (S) ethyl 2-methylthio-4-(3-tert.butylamino-2-hydroxypropoxy)thiazole-5-carboxylate (5.2 g., 0.015 m) MeOH (90 ml.) and liquid ammonia (33 g.) are heated to yield 0.9 g. (14%) of (S) 5-carbamoyl-2-methylthio-4-(3-tert.butylamino-2-hydroxypropoxy)thiazole hydrogen maleate salt, m.p. 180°-2° C.

EXAMPLE 6

5

Carbamoyl-2-methyl-4-(3-tert.butylamino-2-hydroxypropoxy)thiazole hydrogen maleate salt hemihydrate A. Using the procedure of Example 2A, ethyl 4-hydroxy-2-methylthiazole-5-carboxylate (9.35 g., 0.05 m), DMF (100 ml.), NaH (57% mineral oil, 2.5 g., 0.052 m) and the tosylate of 2-phenyl-3-tert.butylamino-2-hydroxymethyloxazolidine (0.053 m) in DMF (100 ml.) are reacted to yield 4.7 g. (30%) of ethyl 2-methyl-4-(3-tert.butylamino-2-hydroxypropoxy)thiazole-5-carboxylate.

B. Using the procedure of Example 2B, ethyl 2-methyl-4-(3-tert.-butylamino-2-hydroxypropoxy)thiazole-5-carboxylate (4 g., 0.014 m), MeOH (90 ml.) and liquid $NH_3$ (33 g.) are heated to yield 1.3 g. (22%) of 5-carbamoyl-2-methyl-4-(3-tert.butylamino-2-hydroxypropoxy)thiazole hydrogen maleate salt hemihydrate, m.p. 177°-78° C.

EXAMPLE 7

(S)

5-Carbamoyl-2-methyl-4-(3-tert.butylamino-2-hydroxypropoxy)thiazole hydrogen maleate salt A. Using the procedure of Example 2A, ethyl 4-hydroxy-2-methylthiazole-5-carboxylate (28 g., 0.15 m), DMF (500 ml.), NaH (50% mineral oil, 7.5 g., 0.16 m) and the tosylate of (S) 2-phenyl-3-tert.butylamino-5-hydroxymethyloxazolidine (0.15 m) in DMF (100 ml.) are reacted to yield 9.8 g. (20%) of (S) ethyl 2-methyl-4-(3-tert.butylamino-2-hydroxypropoxy)thiazole-5-carboxylate.

B. Using the procedure described in Example 2B, (S) ethyl 2-methyl-4-(3-tert.butylamino-2-hydroxypropoxy)thiazole-5-carboxylate (9.8 g., 0.034 m), methanol (185 ml.) and liquid NH$_3$ (8.5 g.) are heated to yield 3.6 g. (29%) of (S) 5-carbamoyl-2-methyl-4-(3-tert.butylamino-2-hydroxypropoxy)thiazole hydrogen maleate salt, m.p. 161°–163° C.

EXAMPLE 8

(S) 5-Cyano-2-methyl-4-(3-tert.butylamino-2-hydroxypropoxy)thiazole hydrogen maleate salt Using the procedure described in Example 3, triphenylphosphine oxide (2.78 g., 0.01 m) in CH$_2$Cl$_2$ (20 ml.), and (S) 5-carbamoyl-2-methyl-4-(3-tert.butylamino-2-hydroxypropoxy)thiazole (1.4 g., 0.005 m) are reacted to yield 0.9 g. (47%) of (S) 5-cyano-2-methyl-4-(3-tert.butylamino-2-hydroxypropoxy)thiazole hydrogen maleate salt, m.p. 172°–174° C.

EXAMPLE 9

(S) 5-Methyl-2-(4'-pyridyl)-4-(3-tert.butylamino-2-hydroxypropoxy)thiazole

Using the procedure in Example 2A, 4-hydroxy-5-methyl-2-(4'-pyridyl)thiazole (3.65 g., 0.019 m), DMF (50 ml.), NaH (57% mineral oil, 0.95 g., 0.02 m) and the tosylate of (S) 2-phenyl-3-tert.butylamino-5-hydroxymethyloxazolidine (0.02 m) in DMF (20 ml.) are reacted to yield 0.6 g. (10%) of (S) 5-methyl-2-(4'-pyridyl)-4-(3-tert.butylamino-2-hydroxypropoxy)thiazole, m.p. 102–104.

EXAMPLE 10

(S) Ethyl 4-(3-tert.butylamino-2-hydroxypropoxy)thiazole-5-carboxylate hydrogen maleate salt hemihydrate To a solution of (S) ethyl 2-methylthio-4-(3-tert.butylamino-2-hydroxypropoxy)thiazole-5-carboxylate (3.6 g., 0.01 m) in 3 N HCl (20 ml.) is added portionwise with stirring zinc dust (2.6 g.). After 3.5 hours at room temperature, the mixture is poured into saturated Na$_2$CO$_3$. The suspension is filtered and the filter pad washed well with CHCl$_3$. The aqueous layer is extracted with CHCl$_3$ (3×75 ml.). The combined CHCl$_3$ extracts are dried over Na$_2$SO$_4$, filtered and concentrated to dryness. The residue is chromatographed on silica gel and the product eluted with CHCl$_3$ saturated with aqueous ammonia. The crude product is crystallized with maleic acid in EtOH-Et$_2$O to yield 0.4 g. (9%) of (S) ethyl 4-(3-tert.butylamino-2-hydroxypropoxy)thiazole-5-carboxylate hydrogen maleate salt hemihydrate, m.p. 103°–105° C.

EXAMPLE 11

(S) 5-Carbamoyl-4-(3-tert.butylamino-2-hydroxypropoxy)thiazole

Using the procedure described in Example 10, (S) 5-carbamoyl-2-methylthio-4-(3-tert.butylamino-2-hydroxypropoxy)thiazole (1.7 g., 0.005 m), 3 N HCl (10 ml.) and zinc dust (0.94 g.) are reacted. Extraction of the aqueous layer with ether yielded unreacted starting material while extraction next with CHCl$_3$ yielded 0.7 g. (48%) of 5-carbamoyl-4-(3-tert.butylamino-2-hydroxypropoxy)thiazole.

EXAMPLE 12

(S) 5-Cyano-4-(3-tert.butylamino-2-hydroxypropoxy)thiazole hydrogen maleate salt Using the procedure described in Example 3, triphenylphosphine oxide (1.42 g., 0.005 m) in CH$_2$Cl$_2$ (10 ml.), triflic anhydride (0.78 ml., 0.005 m) in CH$_2$Cl$_2$ (10 ml.) and (S) 5-carbamoyl-4-(3-tert.butylamino-2-hydroxypropoxy)thiazole (0.7 g., 0.0026 m) are reacted to yield 0.18 g. (19%) of (S) 5-cyano-4-(3-tert.butylamino-2-hydroxypropoxy)thiazole hydrogen maleate salt, m.p. 168°–170° C.

Claims to the invention follow.

What is claimed is:

1. Compounds having the formula

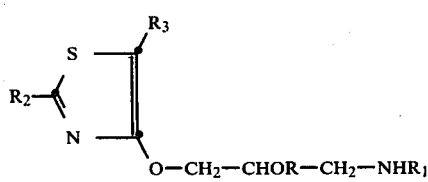

O—CH$_2$—CHOR—CH$_2$—NHR$_1$ and pharmaceutically acceptable salts thereof, wherein R is hydrogen, C$_2$–C$_{12}$ alkanoyl benzoyl, naphthoyl, methylbenzoyl or phenylbenzoyl, R$_1$ is C$_1$–C$_{12}$ alkyl, R$_2$ is hydrogen, CF$_3$, C$_6$–C$_{10}$ carbocyclic aryl selected from phenyl, methylphenyl, halophenyl, nitrophenyl, methoxyphenyl, indanyl and naphthyl, C$_1$–C$_6$ alkyl, C$_1$–C$_6$ alkylthio, C$_1$–C$_6$ alkylsulfinyl, C$_1$–C$_6$ alkylsulfonyl, thienyl and furfuryl, R$_3$ is C$_1$–C$_6$ alkyl, —COOC$_1$–C$_6$ alkyl, COOC$_6$–C$_{12}$ aryl, or C$_6$–C$_{10}$ carbocyclic aryl wherein aryl is selected from phenyl, methylphenyl, biphenylyl and indanyl cyano or CF$_3$ provided that when R$_2$ is phenyl, R$_3$ is other than C$_1$–C$_6$ alkyl or COOC$_1$–C$_6$ alkyl.

2. Compounds of claim 1 wherein R is hydrogen.

3. Compounds of claim 2 wherein R$_1$ is C$_3$–C$_4$ branched chain alkyl.

4. Compounds of claim 3 wherein R$_2$ is C$_1$–C$_6$ alkyl.

5. Compounds of claim 3 wherein R$_2$ is C$_6$–C$_{10}$ carbocyclic aryl.

6. Compounds of claim 3 wherein R$_2$ is C$_1$–C$_6$ alkylthio.

7. Compounds of claim 6 wherein R$_3$ is —COOC$_2$H$_5$.

8. Compounds of claim 3 wherein R$_3$ is CN, or C$_1$–C$_6$ alkyl.

9. Compounds of claim 8 wherein R$_3$ is —CN.

10. Compounds of claim 3 wherein R$_1$ is t-butyl, R$_2$ is phenyl and R$_3$ is —CN.

11. The compounds of claim 3 wherein R$_1$ is t-butyl, R$_2$ is CH$_3$—S— and R$_3$ is —COOC$_2$H$_5$.

12. The compounds of claim 3 wherein R$_1$ is t-butyl, R$_2$ is —CH$_3$ and R$_3$ is —CN.

13. The compounds of claim 3 wherein R$_1$ is t-butyl, R$_2$ is H and R$_3$ is —CN.

14. Compounds of claim 1 having the S-isomer configuration.

15. A pharmaceutical composition for effecting β-adrenergic blockade containing an effective amount of a compound of claim 1 and conventional compounding ingredient.

16. A pharmaceutical composition for effecting immediate human antihypertensive response containing a compound of claim 1 having the formula

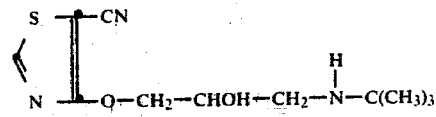

and conventional compounding ingredient.

17. A method for effecting β-adrenergic blockade in a human which comprises administering an effective amount of a composition of claim 15.

18. A method for producing immediate onset antihypertensive in humans which comprises administering an effective amount of claim 16 composition.

* * * * *